US00PP17271P2

(12) United States Plant Patent

Schoenmakers

(10) Patent No.: US PP17,271 P2

(45) Date of Patent: Dec. 12, 2006

(54) *FITTONIA* PLANT NAMED 'RED ANGEL'

(50) Latin Name: *Fittonia verschaffeltii*
Varietal Denomination: Red Angel

(75) Inventor: Kees Schoenmakers, Haaren (NL)

(73) Assignee: Schoenmakers Tropische Potcultures, Haaren (NL)

( * ) Notice: Subject to any disclaimer, the term of this patent is extended or adjusted under 35 U.S.C. 154(b) by 11 days.

(21) Appl. No.: 11/172,360

(22) Filed: Jun. 30, 2005

(51) Int. Cl.
*A01H 5/00* (2006.01)

(52) U.S. Cl. ..... Plt./373

(58) Field of Classification Search ..... Plt./373
See application file for complete search history.

(56) References Cited

U.S. PATENT DOCUMENTS

PP4,516 P * 4/1980 Engelmann ..... Plt./373
PP4,602 P * 10/1980 Cobia ..... Plt./373

OTHER PUBLICATIONS

UPOV ROM GTITM Computer Database, GTI Jouve Retrieval Software 2005/05 Citations for 'Red Angel'.*

* cited by examiner

*Primary Examiner*—Wendy Haas

(57) ABSTRACT

A new cultivar of *Fittonia* plant named 'Red Angel' that is characterized by small green leaves with red veins.

1 Drawing Sheet

Botanical classification: *Fittonia verschaffeltii.*
Variety denomination: 'Red Angel'.

BACKGROUND OF THE INVENTION

The present invention relates to a new and distinct cultivar of *Fittonia* plant botanically known as *Fittonia verschaffeltii* and hereinafter referred to by the cultivar name 'Red Angel'.

The new cultivar was discovered by the inventor in a cultivated area of Haaren, The Netherlands in 2002. 'Red Angel' was discovered as a naturally occurring whole plant mutation of *Fittonia verschaffeltii* 'Red' (not patented).

Asexual reproduction by terminal cuttings of the new cultivar 'Red Angel' was first done in 2002 in Haaren, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Fittonia* cultivar 'Red Angel'.

1. *Fittonia* 'Red Angel' exhibits small leaves.
2. *Fittonia* 'Red Angel' exhibits green leaves with red veins.

The closest comparison cultivar is the parent plant *Fittonia* 'Red'. The new cultivar 'Red Angel' is distinguishable from 'Red' by the following characteristics:

1. 'Red Angel' has a more compact habit.
2. 'Red Angel' has stronger stem pubescence.

BRIEF DESCRIPTION OF THE DRAWING

The accompanying photograph illustrates the distinguishing traits of *Fittonia* 'Red Angel'. The plant in the photograph shows an overall view of a 12 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Fittonia* cultivar named 'Red Angel'. Data was collected in Haaren, The Netherlands from 12 week old greenhouse grown plants in 8.5 cm. containers. The time of year was Spring and the average temperature was 24 degrees Centigrade during the day and 22 degrees Centigrade at night. No photoperiodic treatments were used. Color determinations are in accordance with The Royal Horticultural Society Colour Chart 2001 edition, except where general color terms of ordinary dictionary significance are used. The growing requirements are similar to the species. 'Red Angel' has not been tested under all possible conditions and phenotypic differences may be observed with variations in environmental, climatic, and cultural conditions, however, without any variance in genotype.

Botanical classification: *Fittonia verschaffeltii 'Red Angel'.*
Use: Ornamental.
Parentage: 'Red Angel' is a naturally occurring whole plant mutation of *Fittonia* 'Red'.
Vigor: Moderate.
Growth rate: Moderate.
Growth habit: Broad spreading, upright.
Plant shape: Flattened globular.
Suitable container size: 8.5 cm. diameter container.
Height: Average 6.4 cm.
Width: Average 10.3 cm.
Hardiness: USDA Zone 10.
Propagation: Terminal cuttings.
Time to initiate roots: Approximately 21 days to produce roots on an initial cutting at 24 degrees Centigrade.
Time to produce a rooted cutting: Approximately 35 days to produce a rooted cutting at 24 degrees Centigrade.
Crop time: 12 weeks.

Root system: Fine and fibrous.

Stem:

*Branching habit.*—Freely branching.

*Average number of lateral branches.*—3.

*Pinching.*—Not needed.

*Lateral branch diameter.*—2.5 mm. in diameter.

*Lateral branch length.*—3.7 cm. in length.

*Lateral branch strength.*—Moderate.

*Stem color.*—166A.

*Pubescence.*—Dense, length 1.5 mm, color N155A.

*Internode length.*—1.7 cm. between nodes.

*Internode color.*—144B.

*Shape.*—Rounded, dull.

*Surface.*—Dull.

*Stem strength.*—Moderate.

Foliage:

*Leaf arrangement.*—Opposite.

*Compound or single.*—Single.

*Leaf shape.*—Elliptic, slightly curved.

*Leaf apex.*—Rounded to bluntly acute.

*Leaf base.*—Attenuate.

*Leaf texture.*—Glabrous, slightly rugose, prominent venation.

*Leaf length.*—Average 4.4 cm. in length.

*Leaf width.*—2.1 mm. in width.

*Quantity of leaves per lateral branch.*—Average 6.

*Pubescence.*—Short hairs on margins, 0.5 mm. in length, N155A.

*Leaf margin.*—Entire and slightly repand.

*Vein pattern.*—Pinnate.

*Young leaf color, (upper surface).*—139A.

*Young leaf color, (lower surface).*—147B.

*Mature leaf color, (upper surface).*—139A.

*Mature leaf color, (lower surface).*—Between 138A and 147B.

*Vein color (upper surface).*—51A, lighter towards base 49C to 49D.

*Vein color (lower surface).*—147B to 147C, slightly tinted red towards the leaf margins.

*Leaf attachment.*—Petiolate.

*Petiole dimensions.*—Average 1.5 cm. in length, 2 mm. in diameter, 1.5 mm. in height.

*Petiole color (upper surface).*—177A to 177B.

*Petiole color (lower surface).*—147B to 147C, slightly reddish towards base, 178B to 178C.

*Durability of foliage to stress.*—High.

Flowers: Flowers have not been observed.

Disease and insect resistance: Plants of the new *Fittonia* have not been observed for disease or insect resistance.

It is claimed:

1. A new and distinct variety of *Fittonia* plant named 'Red Angel' as described and illustrated.

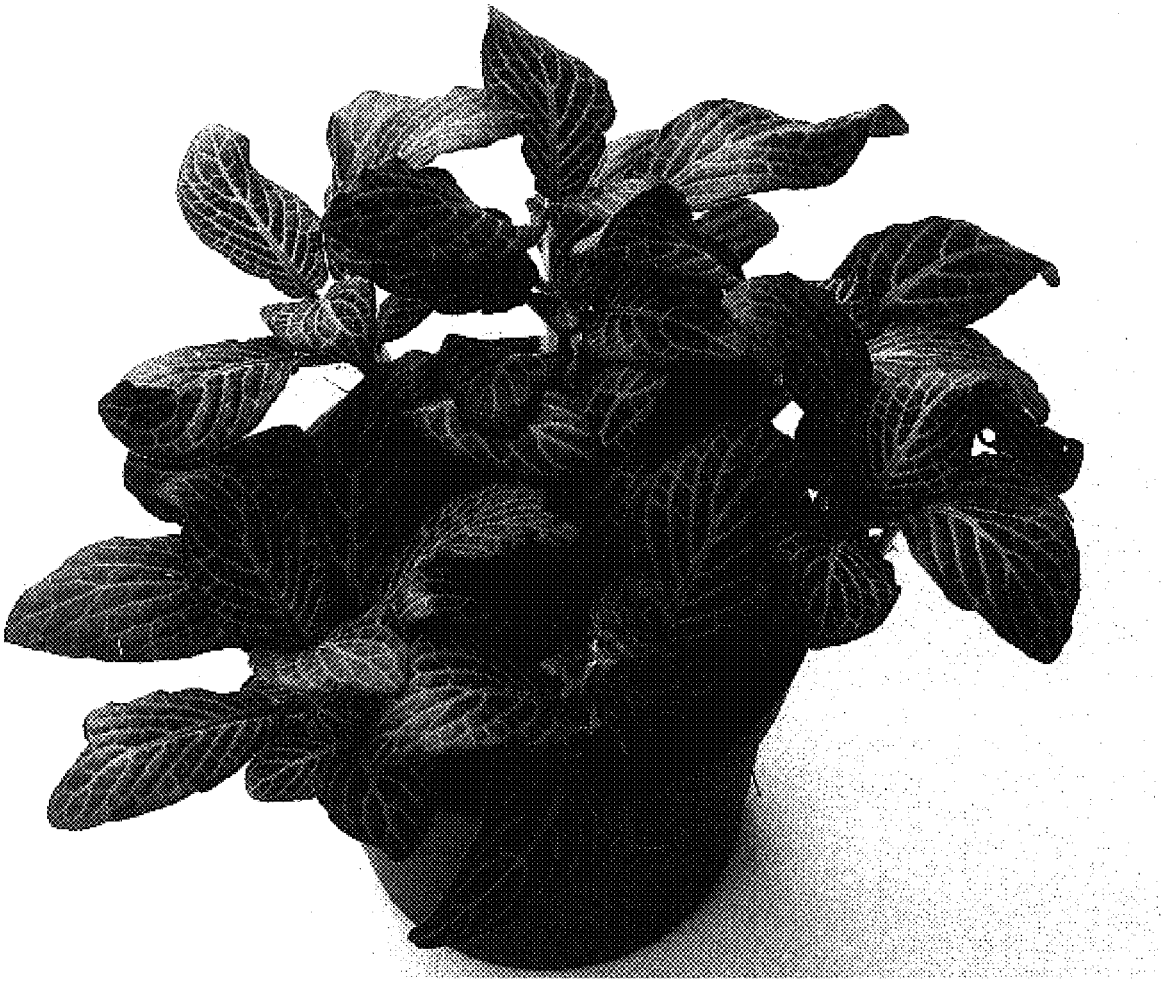

* * * * *